United States Patent [19]
Homma et al.

[11] Patent Number: 4,962,360
[45] Date of Patent: Oct. 9, 1990

[54] SENSOR FOR ELECTROCHEMICAL MEASUREMENT AND METHOD FOR DIAGNOSING CORROSION PROTECTIVE PROPERTIES OF METAL SURFACE COATING BY USING THE SENSOR

[75] Inventors: Koji Homma; Hiroshi Kihira; Satoshi Ito; Kazumi Matsuoka; Noriyuki Hirosawa, all of Kawasaki, Japan

[73] Assignee: Nippon Steel Corporation, Tokyo, Japan

[21] Appl. No.: 354,663

[22] Filed: May 22, 1989

[30] Foreign Application Priority Data

May 24, 1988 [JP] Japan .................. 63-126242

[51] Int. Cl.$^5$ ...................... G01N 27/02; G01N 17/00
[52] U.S. Cl. .................... 324/700; 324/718; 324/559; 324/446; 204/421
[58] Field of Search ............... 204/421, 422; 324/700, 324/718, 514, 559, 558, 557, 446

[56] References Cited

U.S. PATENT DOCUMENTS

| | | | |
|---|---|---|---|
| 3,106,677 | 10/1963 | Edgard | 324/559 |
| 3,343,081 | 9/1967 | Lane | 324/558 |
| 4,197,176 | 4/1980 | Ensanian | 324/71.1 |
| 4,806,849 | 2/1989 | Kihira | |

FOREIGN PATENT DOCUMENTS 6000751  6/1985 Japan .

OTHER PUBLICATIONS

Kihira: "A New Method to Monitor Corrosion . . . "-ASTM Symposium on Degradation of Metals-May 1986.

Primary Examiner—Reinhard J. Eisenzopf
Assistant Examiner—Jose M. Solis
Attorney, Agent, or Firm—Pollock, Vande Sande & Priddy

[57] ABSTRACT

A sensor for electrochemical measurement is disclosed which includes a chamber made of an electrically insulative material and having an open end portion, a super absorbent polymer material filled in the chamber and absorbing at a selected rate a liquid electrolyte, an electrode disposed in the chamber, and a screen which covers the open end portion of the chamber and which prevents the super absorbent polymer material from dropping out from the chamber but permits the liquid electrolyte to transmit through the screen. A method is also disclosed which uses the sensor to measure the degree of degradation of a coating film on metal or the corrosion protective properties of a rust film created on the surface of steel.

11 Claims, 11 Drawing Sheets

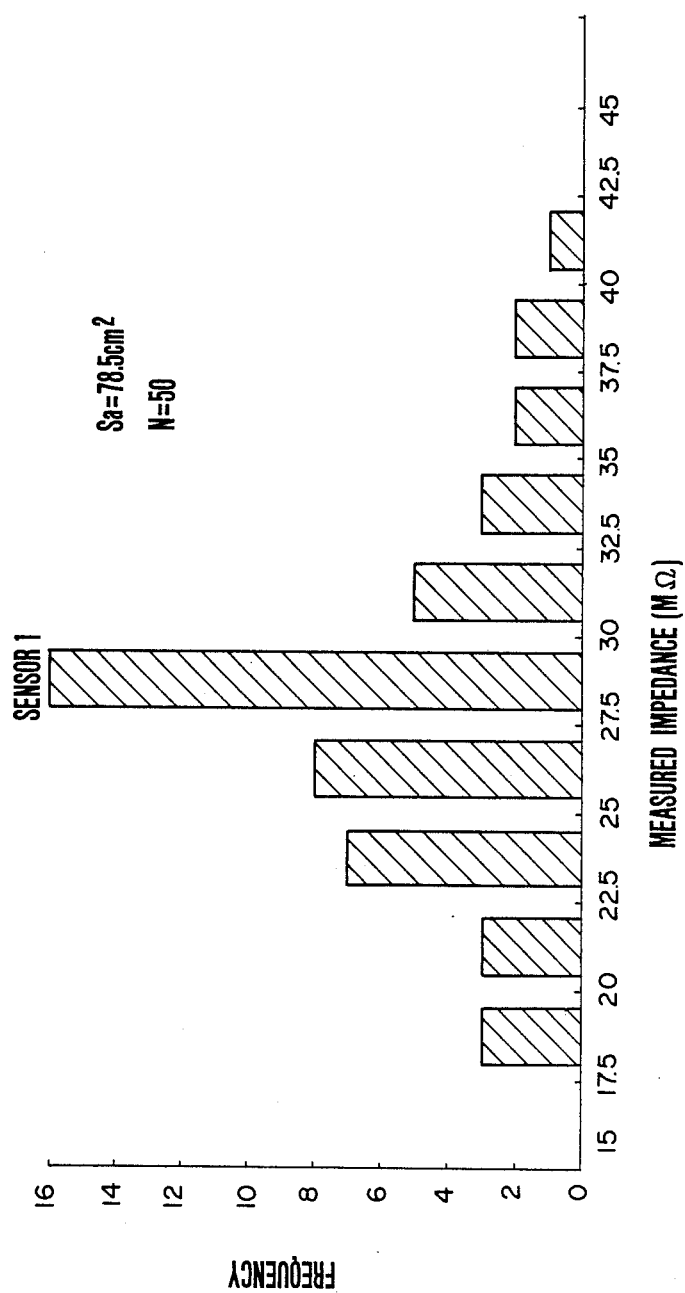

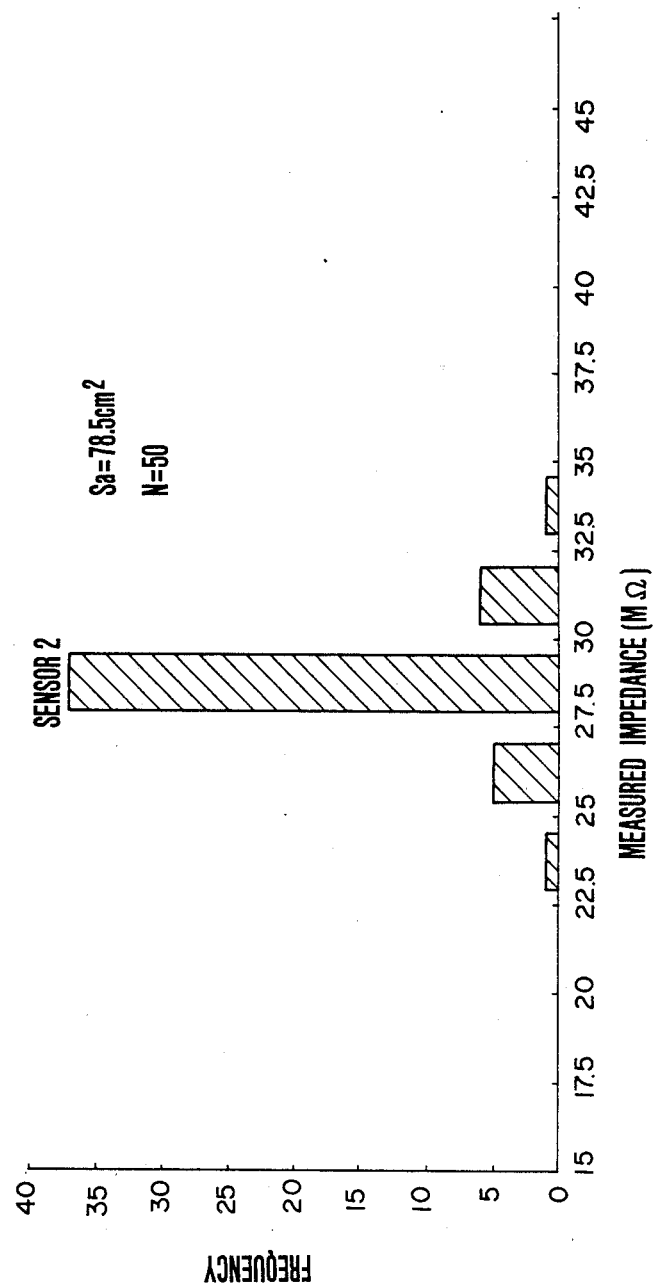

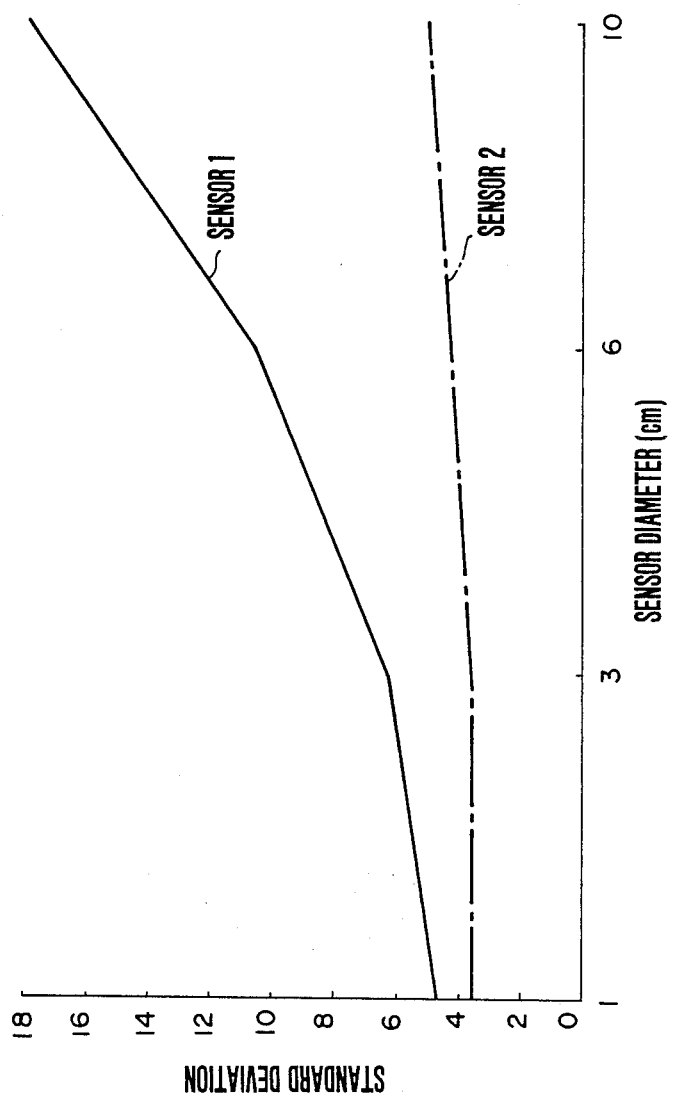

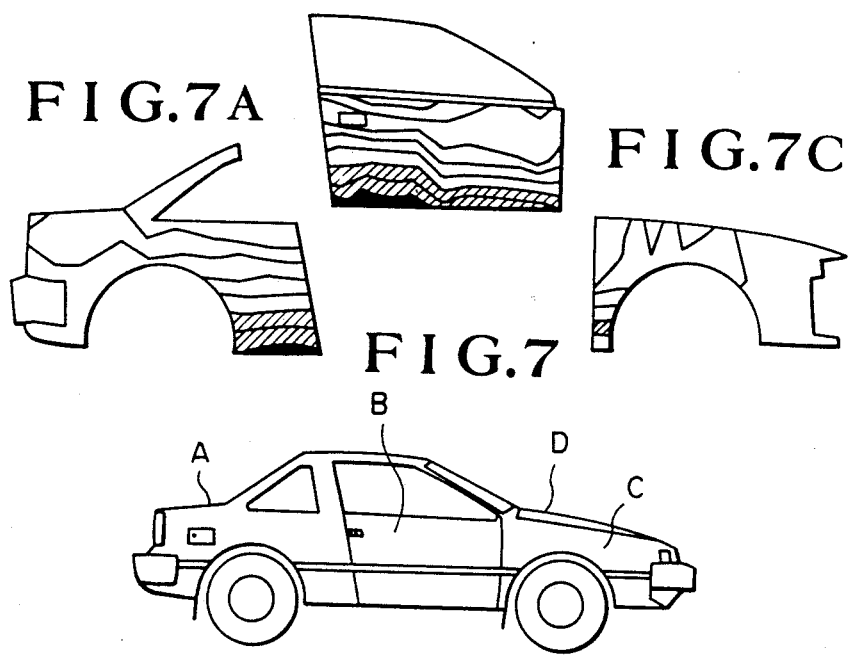
FIG. 7A  FIG. 7B  FIG. 7C  FIG. 7  FIG. 7D
FIG. 7E
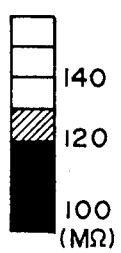
140
120
100
(MΩ)

FIG. 8B
FIG. 8A
FIG. 8C
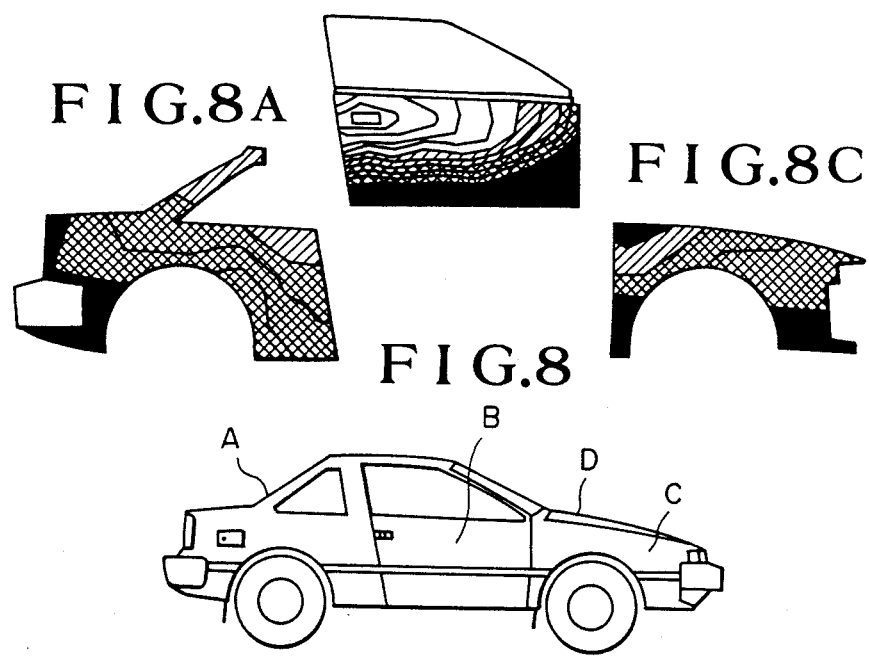
FIG. 8
FIG. 8E
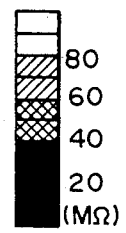
FIG. 8D

SENSOR FOR ELECTROCHEMICAL MEASUREMENT AND METHOD FOR DIAGNOSING CORROSION PROTECTIVE PROPERTIES OF METAL SURFACE COATING BY USING THE SENSOR

BACKGROUND OF THE INVENTION

1. Field of the Invention

This invention relates to a sensor for various types of electrochemical measurement and a method which uses the sensor to measure quantitatively the corrosion protective properties of a coating film on metal or of a rust film created on the surface of steel materials for the purpose of diagnosing the degree of degradation of the coating film and the corrosion protective properties of the rust film.

2. Description of Related Art

In electrochemical measurement wherein an electrode such as a counter electrode or a reference electrode is used to measure potential or current/ voltage characteristics at the surface of a metal material to be measured or impedance at the metal surface under the application of a small AC current for the purpose of measuring the degree of corrosion in the metal surface or the corrosion rate, an electrolyte dissolved in either water or organic solvent or molten salt is used as liquid electrolyte. In any case, the electrochemical measurement using liquid must be carried out in a container such as beaker or cell and has applicability limited to measurement conducted in laboratories.

Therefore, a sensor capable of permitting electrochemical measurement of the surface of metal such as steel materials used in existing structures directly in the field has been proposed by JP-A-62-229056 or the corresponding U.S. Pat. No. 4,806,849 issued to Kihira et al on Feb. 21, 1989 and entitled "Method and Apparatus for Diagnosing Degradation of Coating Film on Metal Material". In the proposal, a cylindrical chamber made of silicon rubber has an open mouth portion in which a sponge impregnated with a liquid electrolyte is filled and when conducting measurement, the open mouth portion is brought into intimate contact with the surface of a metal material to be measured so that the sealing function of the open mouth portion may eliminate a gap through which the liquid electrolyte leaks.

Further, considering that during measurement the liquid electrolyte remains, in great amounts, on the object being measured and evaporation and leakage of the liquid takes place through the sealing portion, the proposed sensor has conveniently an additional liquid electrolyte supplementing apparatus. Moreover, since in diagnosis of an actual structure, non-uniformity of degradation of coating film is found from one location to another, the aforementioned U.S. Patent also proposes a method, by which a great number of points are measured to determine a statistical distribution and a two-dimensional distribution of impedance of the coating film for the purpose of diagnosing quantitatively the degree of degradation of the coating film, as well as simultaneous measurement for efficient implementation of the method by using a plurality of sensors.

On the other hand, there is available a steel material as represented by weathering steel which utilizes a rust film created in natural environment so as to be improved in corrosion resistance. The corrosion protective properties of such a rust film can be diagnosed quantitatively by means of an apparatus as disclosed in JP-A-60-100751 which measures and evaluates AC impedance of the rust film by using two sensors, like the sensor of the aforementioned U.S. Patent, holding a liquid electrolyte.

The electrochemical measurement using the electrolyte in liquid state is convenient for measurement of a sample placed in a container such as beaker but is inconvenient for direct measurement of part of an actual structure in the field because sealing for prevention of leakage of liquid is needed and particularly, it is conducted only at the cost of very degraded efficiency when there are many measurement points.

The conventional sensor for diagnosing the degree of degradation of a coating film on metal faces first of all a problem that the liquid electrolyte tends to leak and adhere to a porfion outside the open mouth portion of the sensor and electric current leaks through the liquid electrolyte remaining at the portion not being under measurement, and a second problem that bubbles remaining in the open mouth portion sometimes cause inequality between the area of the open mouth portion and the actual contacting area and it is rather difficult to mount the sensor without causing variations in contacting area.

Further, to cope with gradual drying of the sponge accommodated in the sensor, the sensor of the aforementioned U.S. Patent employs the additional liquid electrolyte supplementing apparatus which transports the liquid electrolyte under pressure, whereby a proper amount of liquid electrolyte can be supplemented to control wettability and the liquid electrolyte can sufficiently penetrate into the gap at the interface between the surface to be measured and the sensor.

However, when the area of the conventional open mouth portion is increased larger than 1.2 $cm^2$, a liquid electrolyte supplementing apparatus of larger capacity is required and in addition bubbles tend to remain at the interface to make the contacting state unstable resulting in variation of effective contact area, while when the area is decreased smaller than 1.2 $cm^2$, the surface tension creates a droplet which is larger than the area of the open mouth portion and a very small area can not be measured.

When multi-point simultaneous measurement is desired to be conducted by arranging many sensors on an object being measured at a time, many liquid electrolyte supplementing apparatus, identical in number to the sensors, are needed and checking each sensor for its sealing condition and the presence or absence of bubbles at the interface is very laborious and time-consuming.

Incidentally, coated metal is used in a variety of fields of social capital and industrial capital including civil engineering and construction such as bridges, roofs, wall members, tanks, piping and steel towers and transportation equipments such as ships, trains, automobiles and containers. For these structures, coating specifications complying with their purposes are available to offer various kinds of coating films ranging from coating film of relatively low impedance to that of very high impedance.

However, the measurement typically uses a constant pulse current which is small enough not to damage coated films and such a small pulse current generator limits the maximum measurable impedance to about 200 megohms (M ohm). Accordingly, measurable objects are limited and the measurement can be applied to only a painting system of relatively low impedance in which an oil paint is used for the top coating and a red lead paint is used for the ground coating.

In coated metal used for structures, the coated film is considered to be electrically equivalent to a parallel circuit of resistances within the range in which the coated film is considered to be uniform from the standpoint of macroscopic impedance measurement and hence the resistance value measurable by the conventional impedance measuring method increases with increasing of the area of the open mouth of the sensor which is in a range of 1 to 100 cm$^2$.

Therefore, the application of the conventional impedance measuring method would be advantageously extended to a coating system using coat of higher impedance by increasing the area of open mouth of the sensor in the above range. In the conventional method, however, compatibility between the increase in the area of the object to be measured and the steady contacting state of the sensor as well as unimpairment of ease of handling is difficult to achieve.

SUMMARY OF THE INVENTION

An object of this invention is to provide a sensor which can have an open end portion sufficiently large, in area, for measurement of a coating film of high partial impedance and conveniently applicable to rapid multi-point simultaneous measurement, in order that the contacting area can substantially always be constant to exclude a gap at the interface when the open end portion is brought into intimate contact with a coated surface to be measured and leakage of a liquid electrolyte can be prevented in long-term measurement to eliminate the necessity for supplement of the liquid electrolyte.

Another object of this invention is to provide a method for measuring AC impedance of the surface to be measured by using the sensor, for the purpose of diagnosing the degree of degradation of a coating film on the surface of metal or the corrosion protective properties of a rust film created on the surface of metal such as weathering steel.

According to the invention, a sensor for electrochemical measurement comprises a chamber preferably made of a substantially rigid material and having an open end portion suitable for intimate contact with a surface to be measured, at least one of counter electrode and reference electrode which is inserted in the chamber, a super absorbent polymer material filled in the chamber and absorbing a liquid electrolyte, and a water permeable screen provided to cover the open end portion of the chamber and serving to prevent the super absorbent polymer material from dropping out from the open end portion to the outside of the chamber but permit the liquid electrolyte to transmit through the screen.

The type of the electrode inserted in the chamber depends on the kind of electrochemical measurement and for example, for a sensor used for potential measurement, a reference electrode such as silver-silver chloride electrode, hydrogen electrode or calomel electrode is inserted in the chamber and for a sensor used for polarization measurement, in addition to the reference electrode, a counter electrode made of, for example, platinum black or platinized titanium is inserted in the chamber.

In the sensor for electrochemical measurement according to the invention, the effective contacting area with the surface to be measured is maintained substantially constant due to the electrolyte retaining mechanism of the super absorbent polymer and does not vary from one to another sensor. Further, variation of the contact area depending on the user's operating conditions is greatly reduced, thereby ensuring the execution of highly reproducible measurement. Further, since the liquid electrolyte is impregnated in the super absorbent polymer material held in the chamber and leakage of the liquid electrolyte is avoided, the measurement can be carried out many times without supplementing the liquid electrolyte to improve ease of handling when structures of an existing structure are measured in the field and suitability for simultaneous execution of multi-point measurement based on the use of many sensors.

BRIEF DESCRIPTION OF THE DRAWINGS

FIG. 4 is a histogram showing variations of measured values obtained when the same location is measured many times using the prior art sensor.

FIG. 5 is a similar histogram obtained with the sensor of the invention.

FIG. 6 is a graph showing the relation between sensor diameter and deviation of measured values in respect of the prior art sensor and the sensor of the invention.

FIG. 7 is a diagram illustrating an automobile A having surface regions A to D which are used for measurement of the degree of degradation of the coated surface.

FIGS. 7A to 7D are contour line diagrams showing distributions of values of AC impedance measured in the respective regions by using the sensor according to the invention.

FIG. 7E shows the scale of the values in FIGS. 7A to 7D.

FIG. 8 is a diagram illustrating an automobile B having surface regions A to D which are used for measurement of the degree of degradation of the coated surface.

FIGS. 8A to 8D are similar diagrams to FIGS. 7A to 7D.

FIG. 8E is a similar diagram to FIG. 7E.

DESCRIPTION OF THE PREFERRED EMBODIMENTS

Figure 11:
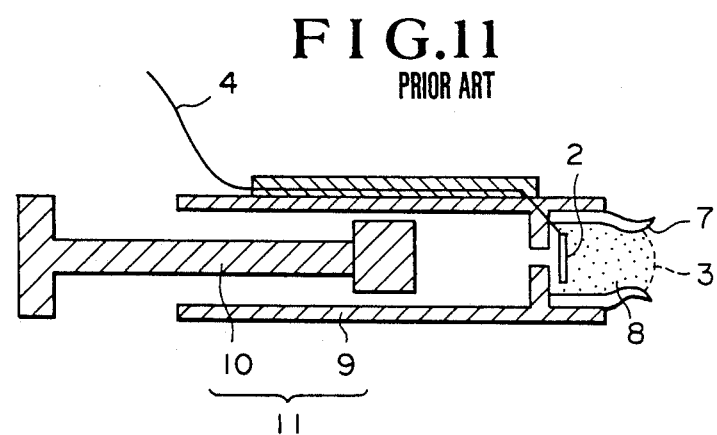
FIG. 11 is a sectional view illustrating the construction of a prior art sensor used for electrochemical measurement.

Prior to describing the construction of a sensor according to the invention, the construction of the sensor disclosed in the aforementioned U.S. Pat. No. 4,806,849 will be described briefly. As shown in FIG. 11, the sensor includes a chamber 8 made of silicon rubber and having an open end mouth portion 7 in which a counter electrode 2 is placed and a sponge 3 impregnated with a liquid electrolyte is filled, the other end portion of the chamber 8 opposite to the open end mouth portion forming a liquid electrolyte supplementing apparatus 11 comprised of a cylinder 9 and a piston 10. Denoted by 4 is a lead wire. As the amount of liquid electrolyte in the chamber 8 decreases, a liquid electrolyte precedently stored in the cylinder 9 is partly pushed by the piston 10 into the chamber 8 to supplement the liquid electrolyte therein. Although the open end mouth portion 7 is made of silicon rubber so as to come into close contact with the surface to be measured during measurement, completely intimate contact can not be obtained and usually the liquid electrolyte must be supplied from the supplementing apparatus 11 to supplement leakage of the liquid each time the measurement starts. In addition, time-consumable works are required for checking the presence or absence of electrolyte leakage around the open mouth of the sensor contacted to the surface to be measured and bubbles at the contact area, especially when the measurements at many points are simultaneously carried out by using many sensors.

Figure 1A:
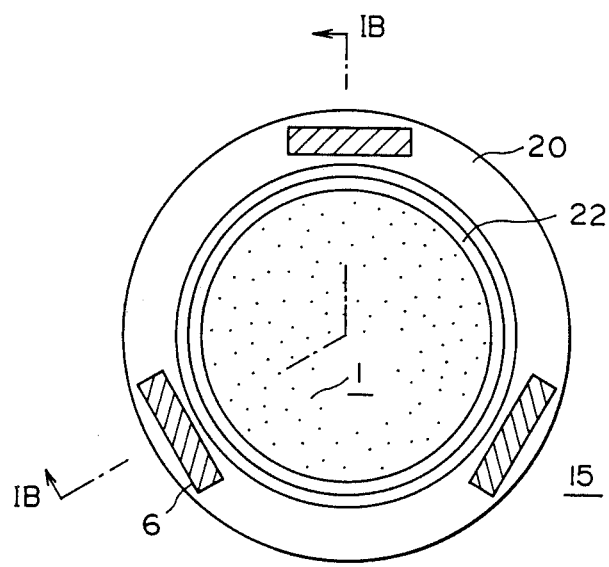
FIG. 1A is a plan view of a sensor for electrochemical measurement according to the invention.
Figure 1B:
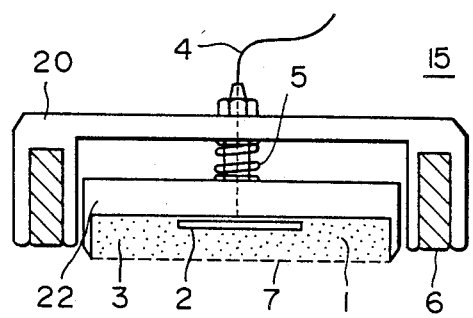
FIG. 1B is a sectional view taken on the line 1B—1B of FIG. 1A.

Referring now to FIGS. 1A and 1B, an embodiment of the sensor for electrochemical measurement according to the invention will now be described. The sensor, generally designated by 15, comprises a cylindrical case 20 made of plastic and having a circumferential open end portion, and a sensor structure mounted in the case 20. Magnet pieces 6 are embedded in the circumferential open end portion of the case 20 so that when the sensor 15 is in use, the open end portion of the sensor may be fixed to a surface being measured of, for example, a steel material under the influence of magnetic force of the magnet pieces. The sensor structure includes a cylindrical chamber 22 made of an electrically insulative, synthetic resin rigid material such as polycarbonate and having an open end portion 7, a counter electrode 2 disposed in the chamber 22, and a super absorbent polymer 1 filled in the chamber 22 and absorbing at a selected rate lower than its saturation or maximum absorbing rate a liquid electrolyte. The electrolyte absorbed in the super absorbent polymer in such a manner comes out upon application of suitable pressure to the polymer. Provided to the open end portion 45 of the chamber 22 is a water permeable screen 7 which serves to prevent the super absorbent polymer from dropping out but permit the liquid electrolyte to transmit through the screen. The chamber 22 is mounted to the case 20 through a spring 5 such that its open end portion slightly protrudes beyond the open end portion of the case 20. Therefore, when the open end portion of the case 20 is pushed against the surface to be measured, the open end portion 7 of the chamber 22 is in contact with the surface to be measured under a specific pressure by the action of the spring 5. The spring force of the spring 7 is selected so that the super absorbent polymer filled in the chamber is pressed against the surface thereby causing the electrolyte to come out. The counter electrode 2 is connected by a lead wire 4 to an external measuring apparatus. The open end portion 7 is formed to have a knife-edge circumference which makes line contact to the surface being measured.

The screen covering the open end portion has the form of a mesh which can withstand expansion pressure of the super absorbent polymer material absorbing the liquid electrolyte and which is fine enough to prevent the super absorbent polymer material from passing through the screen but permit the liquid electrolyte to transmit therethrough and preferably, it is made of highly fungus preventive and biodegradation-proof synthetic fiber such as nylon fiber, polyester fiber, acryl fiber or vinylon fiber.

The super absorbent polymer material used in the invention is non-electrolyte resin of, for example, polyethyleneoxid or polyvinylalcohol system or is electrolyte resin of, for example, polyacrylic acid, sulfonated polystyrene or maleic acid anhydride system, having a saturation or maximum absorbing rate of 10 to 1000 (g/g), when represented by the amount (g) of water absorbed by one gram of resin. Typically, the maximum absorbing rate is 20 to 500 (g/g) for the non-electrolyte resin and 300 to 1000 (g/g) for the electrolyte resin. Such a super absorbent polymer material is used in the form of particles or powder or a carrier of fiber or paper sheet carrying the super absorbent polymer material is used. In the case of particle, the particulate size is 10 $\mu$m to 3 mm at dry state. Table I shows the names, use form and the maximum absorbing rate (g/g) of the super absorbent polymer material used in the invention.

TABLE I

| Raw material system | Form | Max. Absorbing rate (g/g) |
|---|---|---|
| polyacrylic acid system | granular | 300–1,000 |
| vinyl-chloride · acrylic-oxychloride copolymer | " | 500–700 |
| isobutylene · maleic acid anhydride copolymer | " | 200–500 |
| PVA · maleic acid anhydride copolymer | " | 50–300 |
| saponification products of polyacrylonitrile | particle fiber | 80–120 150 |
| polyethylene oxide system | powder | 20–50 |
| starch · acrylonitrile graft polymer | " | 300–1,000 |
| starch · acrylic acid graft polymer | " | 300–1,000 |
| CMC bridging product | powder, non-woven | 50–200 |

Water adsorbed in the super absorbent polymer material exists in the form of bound water, intermediate water and free water and the super absorbent polymer material takes the form of sol or gel depending on whether the water is absorbed at higher or lower rate. In the present invention, the electrolyte is absorbed in the polymer at a rate lower than its maximum absorbing rate so that the polymer is in the form of gel. Thus, by taking advantage of the above characteristics, wettability at the interface between an object to be measured and the super absorbent polymer material can be controlled. Therefore, for example, if the ratio between the mass of the polymer and the mass of the electrolyte absorbed therein is made to be constant, the electrochemical measurement can be carried out under the stable condition to ensure that measurement errors due to the difference in wettability can be eliminated and measurement of high reproducibility can be achieved.

Further, when the super absorbent polymer material absorbs the liquid electrolyte by an amount by which the super absorbent polymer material expands to take a volume slightly larger than the volume of the chamber, intimate contact at the interface between the object to be measured and the sensor can be promoted and bubbles can be excluded completely.

Moreover, since the liquid electrolyte is absorbed in the super absorbent polymer material, the amount of liquid electrolyte consumed during the measurement is very small and by using the sensor of the invention, 100 or more cycles of measurement can be conducted without supplementing the liquid electrolyte in contrast to the prior art measurement wherein the sensor must be supplemented with the liquid electrolyte at the period of each cycle of measurement.

As described previously, the coating film of metal used for structures is electrically equivalent to a circuit of capacitors and resistances and, when only the resistive components are taken, it is equivalent to a simple parallel circuit of resistances. Therefore, for the open end portion area ranging from 1 cm$^2$ to 100 cm$^2$, the maximum measurable impedance of the coating film increases, as the area of the open end portion of the sensor increases. Accordingly, in order to measure impedance of a coating film of higher impedance, the open end portion area of the sensor must be increased. Since in the prior art sensor the contacting area and contacting state between the surface to be measured and the sensor become unstable as the open mouth portion area is increased and stable measurement is difficult to achieve, a practically permissible value of the open mouth portion area is 1.2 cm$^2$ or less. On the other hand, the sensor of the present invention using super absorbent polymer absorbed with electrolyte is in contact with the surface to be measured at a suitable pressure so that the absorbed electrolyte comes out at a suitable degree so as to wet the contact surface uniformly with no bubbles and no leakage of electrolyte around the sensor. Thus, the effective contact area between the sensor and the surface to be measured is maintained substantially constant irrespective of the user's operating conditions and the contacting condition such as wettability at the interface between the measured surface and the sensor is also stable so that even when the open end portion area is increased, the problem encountered in the prior art sensor can be obviated and stable measurement can be conducted even with sensors having the open end portion area which ranges from about 1.2 cm$^2$ to about 100 cm$^2$.

AC impedance of the same location having an area of 78.5 cm$^2$ (diameter = 10 cm) on a surface to be measured of a coated steel material is measured 50 times with the prior art sensor (SENSOR 1) to obtain measured values which vary as shown in a histogram of FIG. 4 and with the sensor of the invention (SENSOR 2) to obtain measured values which vary as shown in a histogram of FIG. 5. Statistic values of the measured data are described in Table II. It will be appreciated from FIGS. 4 and 5 and Table II that the sensor of the invention is highly superior to the prior art sensor in point of stability of measurement.

TABLE II

|  | Sensor 1 (prior art) | Sensor 2 (invention) |
|---|---|---|
| Measurement cycle (frequency) | 50 | 50 |
| Maximum (M Ohm) | 41.7 | 32.6 |
| Minimum (M Ohm) | 18.6 | 24.9 |
| Mean (M Ohm) | 28.1 | 28.8 |
| Median | 28.4 | 28.7 |
| Standard deviation | 5.00 | 1.43 |

Measurement similar to the above is conducted using sensors of the invention and prior art sensors which are differently sized to have different diameters. For each size, the standard deviation is calculated in relation to a mean value of measured values which is normalized to 100, thereby obtaining the relation between sensor diameter and standard deviation $\sigma$ as graphically shown in FIG. 6. As is clear from FIG. 6, while the standard deviation $\sigma$ of the measured values remains substantially unchanged as the sensor diameter increases in the sensor of the invention, the standard deviation increases abruptly as the sensor diameter increases in the prior art sensor to thereby degrade stability. The sensor diameter referred to herein means the diameter of the open end portion of the chamber.

As described above, in accordance with the sensor of the invention, variations in the contacting area between the sensor and the surface to be measured can be reduced to stabilize the contacting condition and in addition, because of elimination of the necessity for supplementing the liquid electrolyte, multi-point simultaneous measurement based on the use of many sensors can be carried out with ease.

Figure 2:
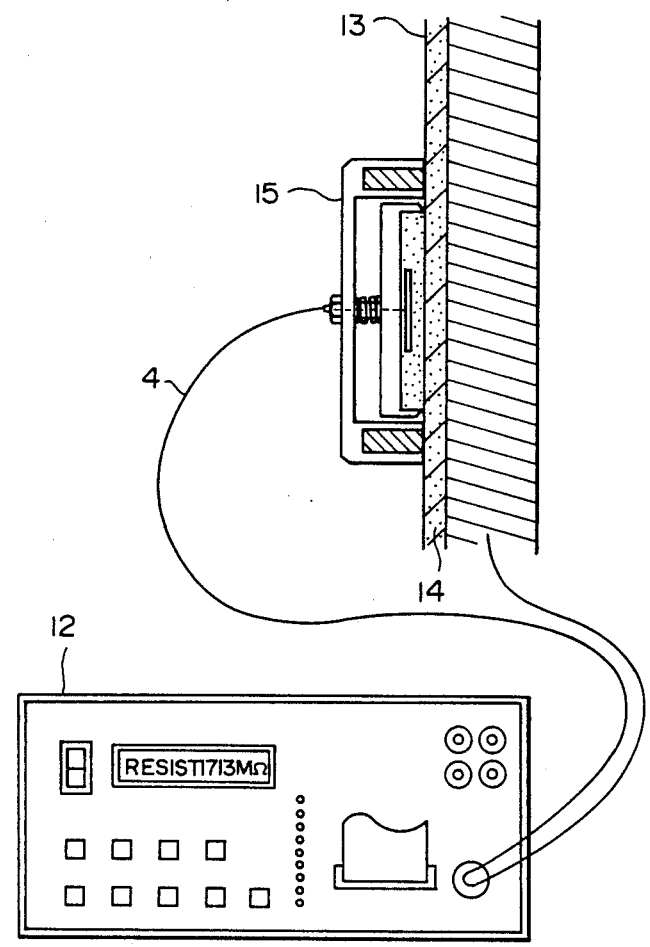
FIG. 2 is a diagram for explaining the overall construction of a measuring apparatus for diagnosing the degree of degradation of a coating film by using the sensor of the invention.

Referring to FIG. 2, a coated metal material such as a steel material 14 covered with a coating film 13 and used for structures can be diagnosed using a sensor 15 of the invention. More particularly, the open end portion of the sensor is brought into contact with the object to be measured and AC impedance is measured directly in the field by means of an AC impedance measuring apparatus 12 electrically connected by lead wires 4 to the opposing electrode and to the metal material standing for the object to be measured. As the AC impedance measuring apparatus, an apparatus disclosed in "A New Method to in situ Monitor Corrosion Protectivity of Rust on Weathering Steel" presented at ASTM "Symposium on Degradation of Metals in the Atmosphere" 12-13, May, 1986, Philadelphia, may be used.

Figure 3:
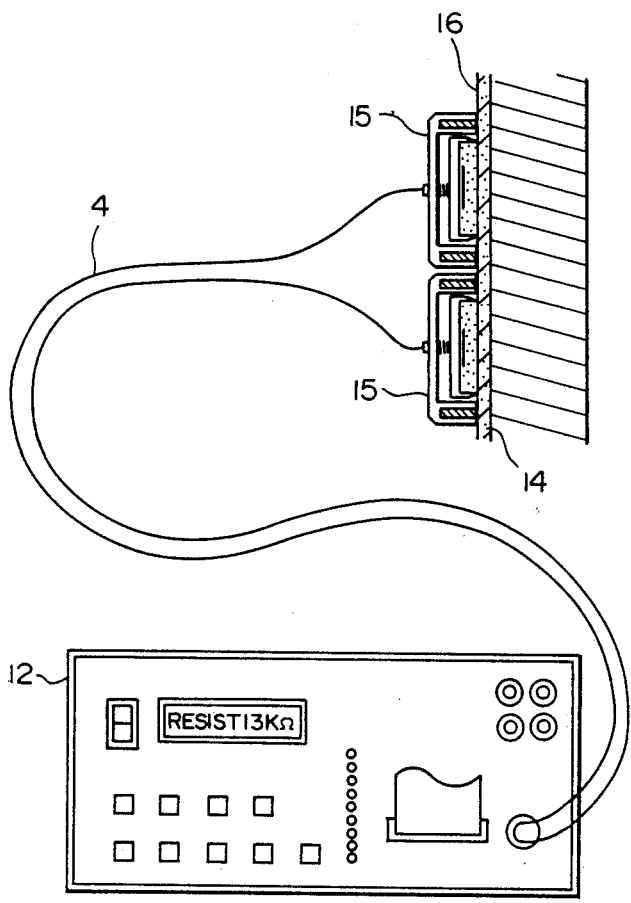
FIG. 3 is a diagram for explaining the overall construction of an apparatus used for multi-point simultaneous measurement based on the use of a plurality of sensors according to the invention, for the purpose of measuring the corrosion protective properties of a rust film on a steel material.

Referring to FIG. 3, a rust film 16 created on a surface 14 of steel is diagnosed using an arrangement illustrated therein.

The range of impedance values for the coating film of coated metal greatly differs from that for the rust film created on the surface of steel but the frequency characteristics for AC impedance resemble for the two kinds of coating films in point of the fact that the corrosion protective properties of either type of coating can be captured at specified frequencies respectively corresponding to the ranges of impedance values.

As an example, frequencies are related to the ranges of impedance as shown in Table III and set in the measuring apparatus.

TABLE III

| Impedance of coating | Optimum frequency |
|---|---|
| 0–20 Ω | 1.7 KHz |
| 20–200 Ω | 850 Hz |
| 200–2 KΩ | 450 Hz |
| 2K–20 KΩ | 250 Hz |
| 20K–2 MΩ | 100 Hz |
| 2M–200 MΩ | 500 mHz |

Specifically, the operation of the invention is featured in that firstly the super absorbent polymer material can reatin the liquid electrolyte for a long time to permit multi-point measurement without supplementing the liquid electrolyte and consequent elimination of the necessity for the liquid electrolyte supplementing apparatus, that secondly even for the area of the measured object being about 100 times increased as compared to that in the prior art, bubbles do not remain between the sensor and the object to be measured to permit stable measurement and consequently a coating film of higher partial impedance can be measured in the field, and that thirdly during the multi-point simultaneous measurement, checking individual sensors for their installation condition is not needed in order that these sensors can be fixed easily without causing leakage of liquid, generation of bubbles and variations in the object area.

While the liquid electrolyte retaining mechanism of the sponge, as used in the conventional sensor, utilizes capillarity function, the super absorbent polymer material takes advantage of adsorption of water molecules to the hydrophilic radical. Therefore, leakage of liquid will not occur even under the application of low level pressure and especially where the object to be measured is a coating film of high partial impedance system, accurate measurement can be achieved efficiently in contrast to the prior art measurement using the sponge wherein a small amount of liquid electrolyte adheres to other area than the contacting area and current flows into the former area to impair accurate measurement.

Fourthly, the polymer in the form of gel can follow the contour of an object to be measured and even when the object is not planar but is curved, measurement of the object can be achieved. This advantage is significant because coated metal used for actual structures is often configured to have a curvature.

Similarly, the advantages of the omission of the liquid electrolyte supplementing apparatus, the prevention of leakage of liquid and the contour follow capability can also be realized in the case of diagnosing the corrosion protective properties of the rust film.

Examples will now be described where the degree of degradation of a coating film on metal used for structures is diagnosed using the electrochemical measurement sensor with super absorbent polymer material according to the invention.

As described previously, a variety of coated metal materials are used for structures but in the following examples, two automobiles are selected which undergo electro-deposition coating specified to coating specifications of relatively high impedance.

The automobiles to be measured are specified by the manufacture date, running distance, coating specifications and use condition which are described in Table IV.

TABLE IV

|  | Automobile A | Automobile B |
| --- | --- | --- |
| Manufacture date | Sho 60, June | Sho 54, Nov. |
| Used period | 2 years and 10 months | 8 years and 5 months |
| Running distance (km) | 25100 | 75000 |
| Coating color | white | white |
| Name and feature of principal place of use | Midori-ku, Yokohama-shi; inland, residential area | Asahi-ku, Yokohama-shi; inland, residential area |
| Fashion of custody | left outdoors | left outdoors |
| Main purpose of use | commuting | leisure for the holidays |
| Maintenance state (interval for car wash) | Once every three month | once every month |

Conditions for measurement will now be described,. The used sensor has the construction shown in FIGS. 1A and 1B, the chamber 22 is made of polycarbonate, the open end portion has a circular form of 80 mm diameter, and the open end portion is covered with the screen in the form of a mesh made of fine acryl fiber of about 100 $\mu$m diameter which is relatively highly absorbent.

A super absorbent polymer material of isobutylene - maleic acid anhydride system absorbing a solution of 0.01 mol sodium sulfate/one solution at an absorbing rate of ten times is filled in the chamber. A platinum wire serving as the counter electrode is inserted in the super absorbent polymer material.

The AC impedance measuring apparatus is connected by lead wires to the counter electrode of the sensor and to a metallic portion, serving as the active electrode, of the coated metal. For example, an exposed metal portion such as a stop block for door lock of the automobile is electrically connected to a metallic portion of the coated metal and is therefore used as the active electrode.

Prior to conducting measurement of the coated metal, resistance of liquid per se is measured by contacting the open end portion of the sensor to a bare, cold rolled steel plate serving as the active electrode to obtain a liquid resistance of 10 ohm/cm$^2$.

Typically, impedance of the coating film having the corrosion protective properties amounts up to several of M ohm/cm$^2$ and therefore the liquid resistance is negligibly small.

In order to capture ion transmission resistance representative of the corrosion protective properties of the coating film, the impedance measuring apparatus is so designed that optimum frequencies obtained from the relation between frequencies and AC impedance characteristics of the coating film are preset as described in Table III and one of the optimum frequencies is automatically selected in accordance with impedance of an object to be measured, and is operable to apply an AC electrical signal in the form of a constant pulse current.

Also, the measuring apparatus is designed to be compact, light and portable to meet measurement in the field in cooperation with the sensor.

The object to be measured is divided into a plurality of regions, A to D in FIG. 7 or FIG. 8, and each region is subjected to multi-point measurement.

Results of the measurement are illustrated for the automobile A in terms of contour line as shown in FIGS. 7A to 7D (respectively corresponding to the regions A to D) with the scale as shown in FIG. 7E and for the automobile B in terms of contour line as shown in FIGS. 8A to 8D (respectively corresponding to the regions A to D) with the scale as shown in FIG. 8E.

Empirical knowledge of the degradation of automobile coating film teaches that the degree of degradation is great especially at portions exposed to chipping during high-speed running, including the fore end portion of the bonnet, the lower portions of the front and rear fenders, the front and rear ends and the lower portions of the doors. Interestingly, no degradation is found and confirmed visually in the automobile A standing for the object to be measured but the contour lines shown in FIGS. 7A to 7D clearly tell such a tendency and in addition, the distribution of degraded portions in the automobile A accurately coincide with the distribution of degraded portions in the automobile B though measured values range from 100 M ohm to 200 or more M ohm for the automobile A but for the automobile B, from 0 to 100 M ohm and the degree of degradation greatly differs for the automobiles A and B.

Figure 9:
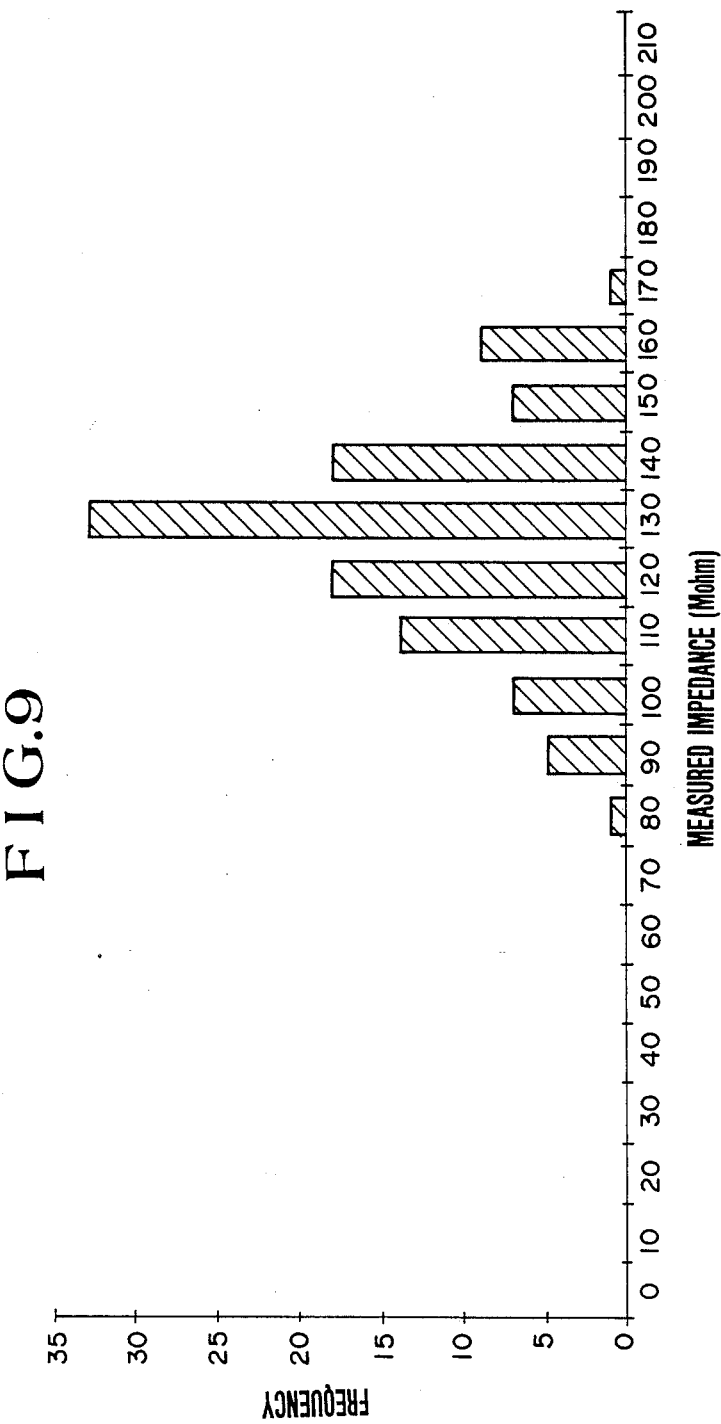
FIGS. 9 and 10 are histograms showing distributions of values obtained with the automobiles A and B, respectively.
Figure 10:
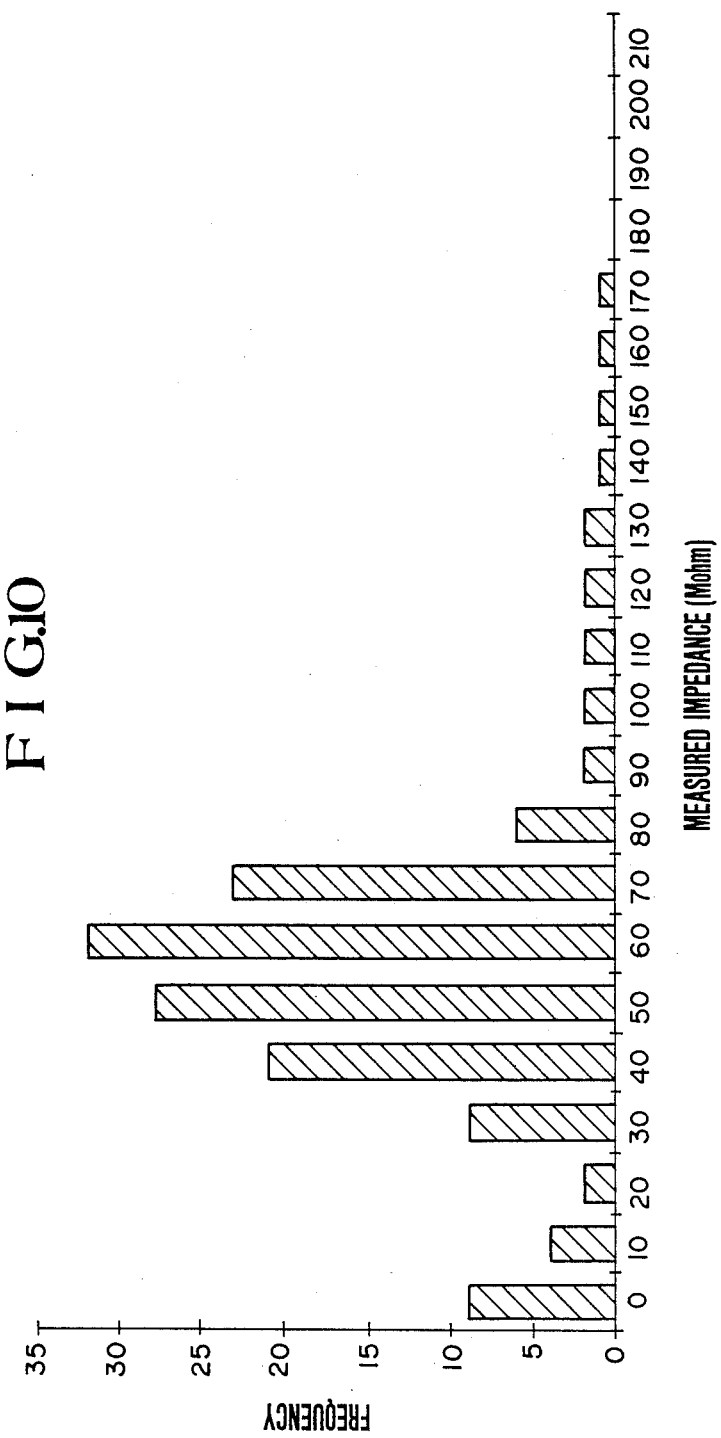

The same location or point is measured many times. A histogram of measured values is illustrated in FIG. 9 for the automobile A and in FIG. 10 for the automobile B. Each histogram is reduced to approximate a normal distribution which provides mean value, median, variance and the like used for diagnosing the degree of degradation of the coating films.

The sensor and the method for diagnosing the degree of degradation of the coating film have been described as being exemplarily applied to automobiles but obviously may also be applied to other objects including coated structures and rust films created on weathering steel.

The present invention can attain the following effects.

(1) In diagnosing coating films on actual structures, the measurement range is extended to a high impedance of coating film which is approximately 100 times the coating film impedance measurable with the prior art sensor.

(2) Bubbles do not remain between the sensor and the object to be measured and leakage of liquid to the outside of an area to be measured does not occur, so that stability of the contacting area can be maintained and measurement of high reproducibility can be ensured.

(3) Elimination of the liquid electrolyte supplementing mechanism can promote ease of handling. Particularly, this effect is significant for the multi-point simultaneous measurement.

(4) The sensor can follow the contour of an object being measured even when the object has a curved surface.

We claim:

1. A sensor for electrochemical measurement comprising:
    a chamber made of an electrically insulative material and having an open end portion adapted to be in contact with a surface to be measured;
    a super absorbent polymer material filled in said chamber and absorbing at a selected rate a liquid electrolyte;
    an electrode disposed in said chamber; and
    open end covering means which covers the open end portion of said chamber and which prevents said super absorbent polymer material from dropping out from said chamber but permits said liquid electrolyte to transmit through said open end covering means.

2. A sensor according to claim 1, wherein the electrolite is absorbed in the super absorbent polymer at a rate equal to or lower than a maximum absorbing rate of the polymer.

3. A sensor according to claim 2 wherein said super absorbent polymer material has a maximum absorbing rate of 10 to 1000 (g/g).

4. A sensor according to claim 3 wherein said super absorbent polymer material is non-electrolyte resin having a maximum absorbing rate of 20 to 500 (g/g).

5. A sensor according to claim 3 wherein said super absorbent polymer material is electrolyte resin having a maximum absorbing rate of 300 to 1000 (g/g).

6. A sensor according to claim 2 wherein said super absorbent polymer material is of particles having a diameter of 10 $\mu$m to 3 mm in dry condition.

7. A sensor according to claim 6 wherein said super absorbent polymer material is electrolyte resin having a maximum absorbing rate of 300 to 1000 (g/g).

8. A sensor according to claim 1 wherein said open end covering means comprises a screen made of synthetic fiber.

9. A sensor according to claim 1, wherein said chamber is made of a rigid material.

10. A method for measuring the degree of degradation of a coating film of a coated metal material, comprising:
    mounting the sensor according to claim 1 on a surface to be measured, covered with a coating film, on metal material such that said open end portion of said sensor makes intimate contact with the surface to be measured; and
    measuring AC impedance of said surface.

11. A method for measuring the corrosion protective properties of a rust film created on a surface of a steel material, comprising:
    mounting the sensor according to claim 1 on a surface to be measured of the steel material having the rust film created on its surface such that said open end portion of said sensor makes intimate contact with the surface to be measured; and
    measuring AC impedance of said surface.

* * * * *